US00PP33098P2

(12) United States Plant Patent
Van Swieten

(10) Patent No.: US PP33,098 P2
(45) Date of Patent: May 25, 2021

(54) ***PHALAENOPSIS* ORCHID PLANT NAMED 'PHALGYMA'**

(50) Latin Name: ***Phalaenopsis* hybrid**
Varietal Denomination: PHALGYMA

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,179

(22) Filed: Nov. 4, 2020

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGYMA', particularly characterized by very light purple, striped flowers with reddish-purple lips, a flat flower shape in lateral view, very short whiskers on the apical lobe of the lip, many branches, and is propagated by meristem tissue culture, is disclosed.

3 Drawing Sheets

Genus and species: *Phalaenopsis* hybrid.
Variety denomination: 'PHALGYMA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGYMA'.

The new *Phalaenopsis* plant is a product of a planned breeding program conducted by the inventor in Bleiswijk, the Netherlands. The objective of this breeding program was to create a new *Phalaenopsis* plant with attractive, small, very light purple, striped flowers with reddish-purple lips, suitable for potted plant production.

The new *Phalaenopsis* plant 'PHALGYMA' is a result of cross-pollination made by the inventor in July 2010 in Bleiswijk, the Netherlands, of the proprietary female, or seed parent, *Phalaenopsis* hybrid '01-0269' (unpatented) with the proprietary male, or pollen parent, *Phalaenopsis* hybrid '33408-09' (unpatented).

The new *Phalaenopsis* was selected by the inventor as a single plant within the progeny of the stated cross-pollination in a controlled greenhouse in Bleiswijk, the Netherlands, in May 2013. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 30, 2019 (Application no. 2019/2059), by Applicant who obtained the subject matter disclosed directly from the inventor. 'PHALGYMA' has not been made publicly available or sold anywhere in the world prior to the effective filing date of this application with the exception of sales or disclosures made one year or less before the effective filing date of this claimed invention by Applicant who obtained 'PHALGYMA' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGYMA' as a new and distinct variety of *Phalaenopsis* plant:

1) Very light purple, striped flowers with reddish-purple lips;
2) Flower shape in lateral view is flat;
3) Apical lobe of the lip has very short whiskers; and
4) Plant has many branches.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in October 2020. Colors in the photographs may differ from the color values cited in the detailed botanical description, which accurately describe the actual colors of the new variety.

DESCRIPTION OF THE NEW VARIETY

Figure 1:
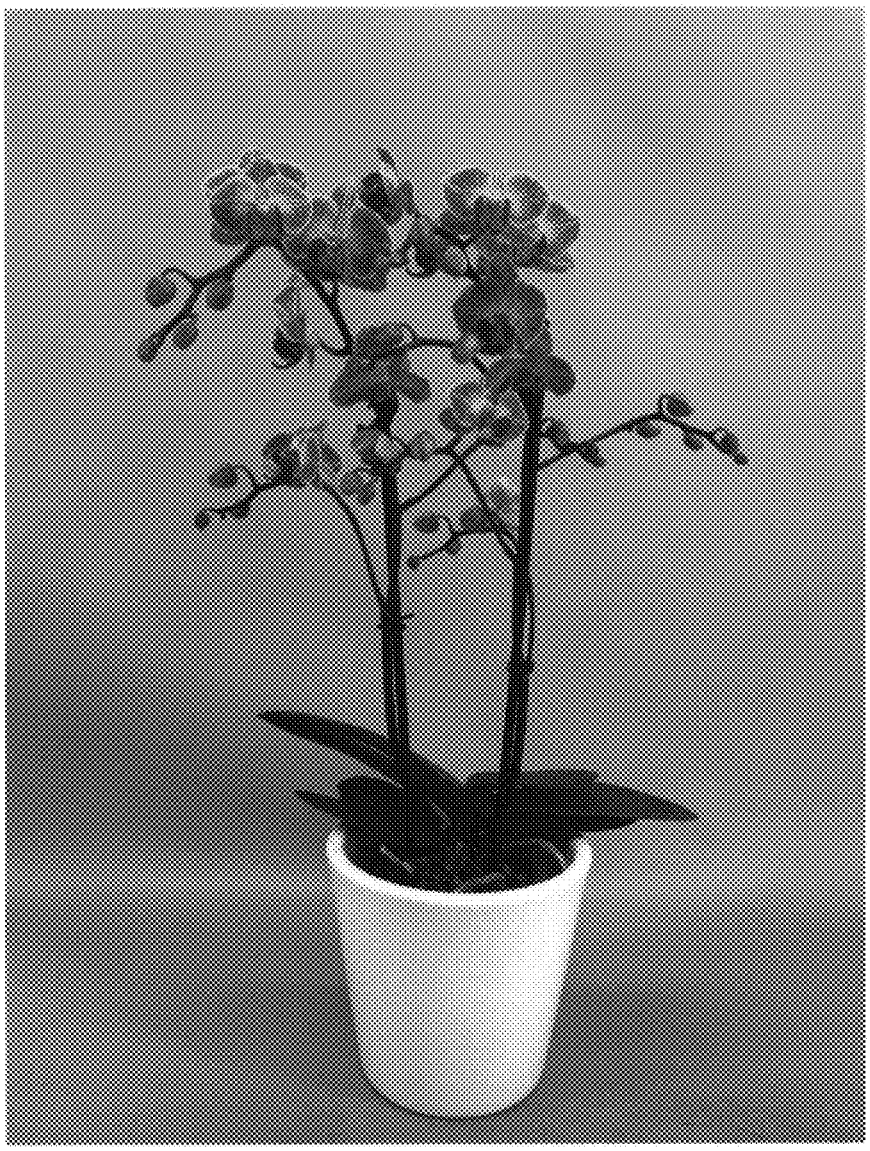
FIG. 1 shows the overall plant habit, including blooms, buds, and foliage of 'PHALGYMA'.
Figure 2:
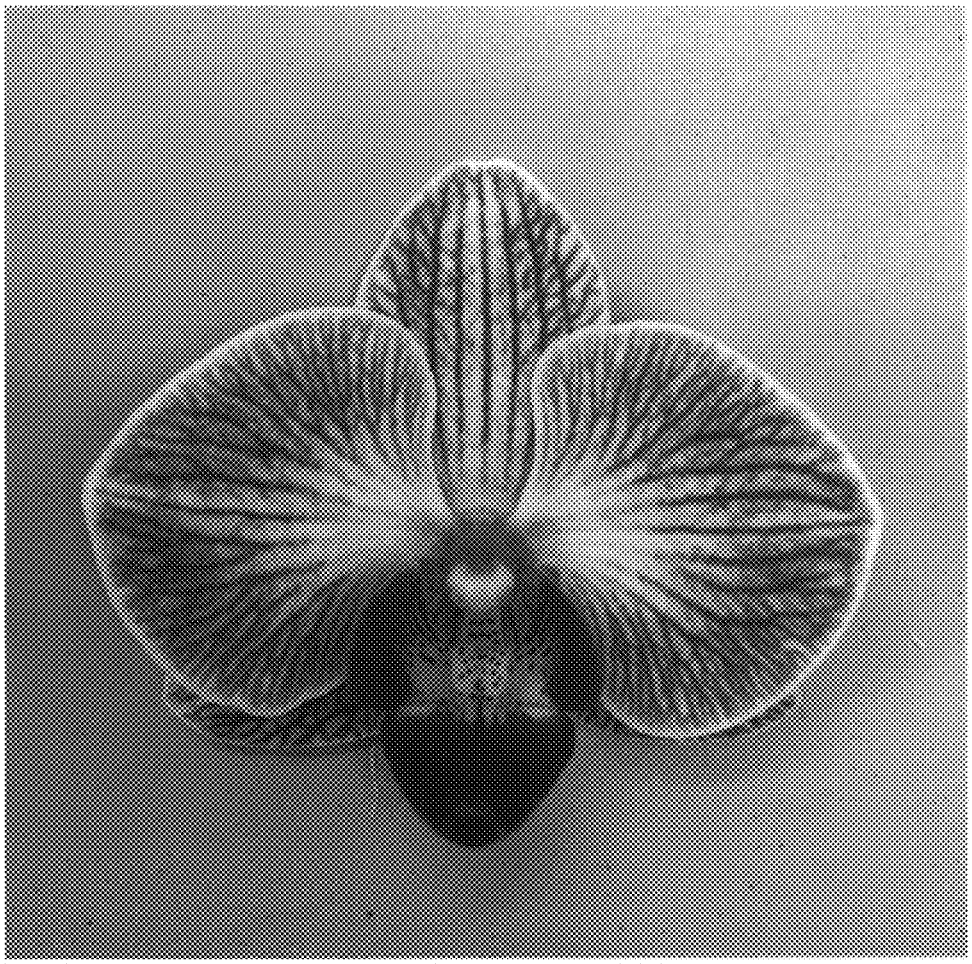
FIG. 2 shows a close-up of a flower of 'PHALGYMA'.
Figure 3:
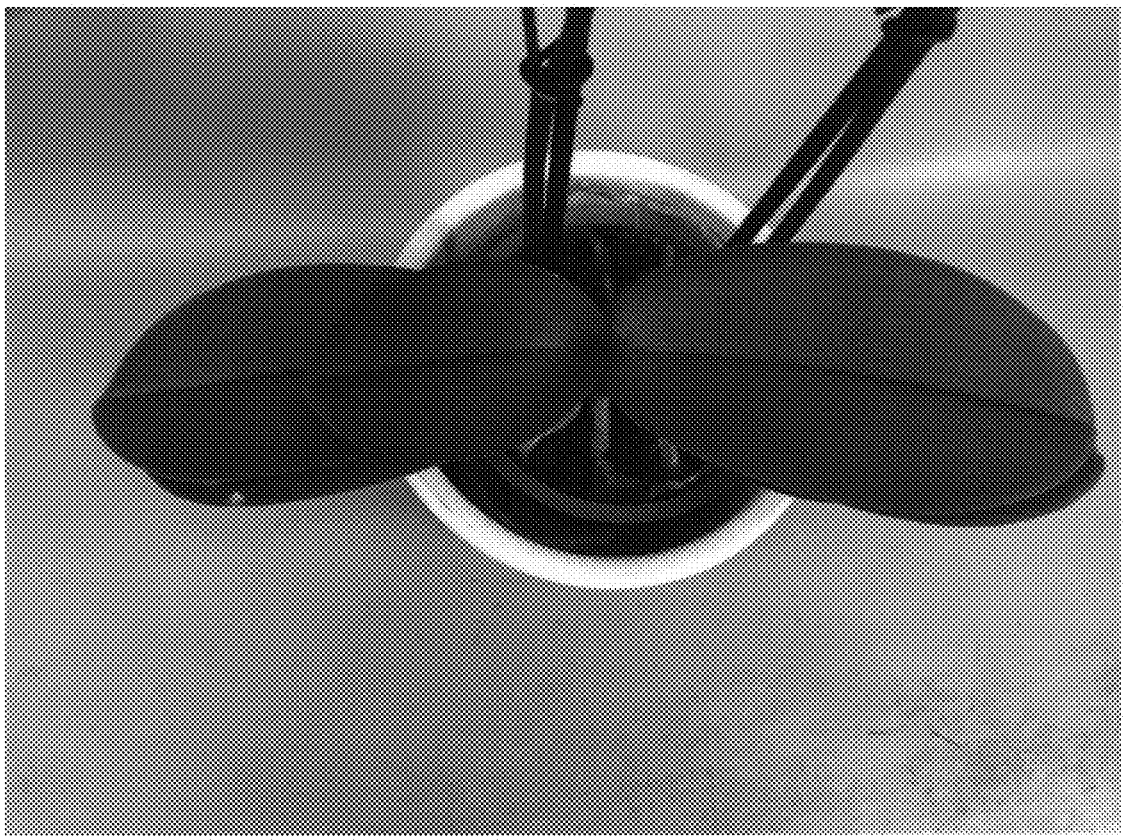
FIG. 3 shows an overhead view of the leaves of 'PHALGYMA'.

The following detailed description sets forth the distinctive characteristics of 'PHALGYMA'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in October 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGYMA'.

Parentage:

*Female parent*.—*Phalaenopsis* cultivar '01-0269' (unpatented).

*Male parent*.—*Phalaenopsis* cultivar '33408-09' (unpatented).

Propagation:

*Type*.—Meristem tissue culture.

Roots:

*Root description*.—Greyed-green (a color in between RHS 190B and 190C) colored roots with branching lateral roots having yellowish-green (RHS N144A) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 40.0 cm to 45.0 cm.

*Width* (*measured from leaf tips*).—About 28.0 cm to 30.0 cm.

*Vigor*.—Strong.

Leaves:

*Mature leaves*.—Quantity per plant: 10 to 12 leaves are produced before flowering. Length (fully expanded): 13.0 cm to 15.0 cm. Width: 6.0 cm to 7.0 cm. Position of the broadest part of the leaf: Toward apex. Shape: Oblong. Base shape: Moderately elongated. Apex: Obtuse unequal. Leaf blade angle with the petiole (measured from the horizontal position): Between 10 degrees and 25 degrees. Leaf margin: Entire. Color: Upper surface: RHS 146A. Lower surface: RHS 146C with a touch of brown (RHS 200C) toward margin. Texture (both upper and lower surfaces): Smooth. Thickness: 2.0 mm to 2.2 mm. Variegation: Absent. Venation: Pattern: Parallel. Color of the midvein: Upper surface: RHS 146A. Lower surface: RHS 146B with a touch of brown (RHS 200C).

Peduncle:

*Quantity per plant*.—1 to 3.

*Number of flowers per peduncle*.—40 to 50.

*Length*.—40.0 cm to 45.0 cm.

*Diameter*.—4.8 mm to 5.3 mm.

*Strength*.—Strong.

*Aspect*.—Upright to slightly pendent.

*Texture*.—Smooth.

*Color*.—Reddish-brown (RHS 200B) with a touch of yellow-green (RHS 146C).

*Internode length*.—2.0 cm to 4.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 280.0 mm to 330.0 mm.

*Flowering time*.—First flowers can be expected 10 to 11 months after planting in a 12-cm pot.

*Flower*.—Height: 42.0 mm to 46.0 mm. Diameter: 50.0 mm to 55.0 mm. Depth of lip: 17.0 mm to 19.0 mm.

*Flower longevity*.—On the plant: 7 to 9 weeks.

*Flower shape*.—Flat.

*Fragrance*.—Absent.

*Flower bud*.—Average size: Medium. Length: 15.0 mm to 17.0 mm. Width: 13.0 mm to 15.0 mm. Shape: Egg shaped. Color: Yellow-green (a color in between RHS 145B and 195B) with a touch of purplish-red (RHS N77B).

*Petals*.—Arrangement: Open/free. Shape: Semi-circular. Apex: Obtuse asymmetric. Margin: Weakly undulated. Length (from base to tip): 23.0 mm to 25.0 mm. Width: 27.0 mm to 29.0 mm. Position of the broadest part of the petal: Toward the base. Color (when fully opened): Upper surface: Basic color: Very light purple (RHS 76B). Over color: Reddish-purple shade (RHS N78B) and stripes (RHS N78A). Lower surface: Basic color: Very light purple (RHS 76B). Over color: Purplish-pink shade (RHS N78C); reddish-purple stripes (RHS N78B). Number of spots and stripes on the petals (upper surface): Many stripes. Color of spots and stripes on the petals (upper surface): RHS N78A. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 25.0 mm to 27.0 mm. Width: 19.0 mm to 21.0 mm. Position of the broadest part of the dorsal sepals: At the middle. Color (when fully opened): Upper surface: Basic color: Light purple (a color in between RHS 76A and 76B). Over color: Reddish-purple stripes (RHS N78A) and netting (a color in between RHS N78A and N78B). Lower surface: Basic color: Very light purple (RHS 76B). Over color: Diluting reddish-purple stripes (a color in between RHS N78B and N78C). Number of spots and stripes on the dorsal sepals (upper surface): Many stripes. Color of spots and stripes on the dorsal sepals (upper surface): RHS N78A. Density of netting of the dorsal sepals (upper surface): Low. Color of the netting: A color in between RHS N78A and N78B.

*Lateral sepals*.—Shape: Ovate. Apex: Obtuse asymmetric. Margin: Entire. Length (from base to tip): 26.0 mm to 28.0 mm. Width: 18.0 mm to 20.0 mm. Position of the broadest part of the lateral sepals: Toward the base. Color (when fully opened): Upper surface: Basic color: Very light purple (a color in between RHS 76B and 76C). Over color: Touch of light yellow-green (RHS 145D) and small dots (RHS 71A) at the base; stripes (RHS N78A). Lower surface: Basic color: Very light purple (RHS 76B). Over color: Light yellow-green (RHS 145D); diluting purplish-pink stripes (RHS N78C). Number of spots, dots, and stripes on the lateral sepals (upper surface): Many stripes and few very small dots at the base. Color of spots, dots, and stripes on the lateral sepals (upper surface): Stripes (RHS N78A); dots (RHS 71A). Density of netting of the lateral sepals (upper surface): None. Color of the netting (upper surface): Not applicable.

*Labellum* (*lip*).—Whiskers: Present. Length of whiskers: 2.0 mm to 4.0 mm. Color of whiskers: Reddish-purple (a color in between RHS N78A and N79C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated (widely wavy). Length: 15.0 mm to 17.0 mm. Width: 10.0 mm to 12.0 mm. Color: Upper surface: Light greenish-yellow (RHS 4B) and white (RHS NN155C) at the base; dark red (RHS 59A) on one side and reddish-purple (RHS N78A) toward the other side. Lower surface: White (RHS NN155C) at the base; dark red (RHS 59A) on one side and reddish-purple (RHS N78A) toward the other side. Number of spots, dots, and stripes on the lateral lobe: Few small dots and stripes at the base. Color of spots, dots, and stripes on the lateral lobe: Dots and stripes (RHS 59A). Density of netting of the lateral lobe: None. Color of the netting: None.

*Apical lobe*.—Shape: Ovate. Margin: Entire. Length: 18.0 mm to 20.0 mm. Width: 13.0 mm to 15.0 mm. Color: Upper surface: Light greenish-yellow (RHS 4C) and hint of white (RHS N155B) at the base; dark purplish-red (RHS N79C) and reddish-purple (a color in between RHS N78A and N79C) toward whiskers. Lower surface: White (RHS N155B) at the middle and reddish-purple (a color in between RHS N78A and N79C) toward margins. Number of spots and stripes on the apical lobe: None. Color of spots and stripes on the apical lobe: Not applicable. Density of netting of the apical lobe: None. Color of the netting: None.

*Callus*.—Average size: Small. Height: 3.0 mm to 4.0 mm. Length: 4.0 mm to 5.0 mm. Width: 3.0 mm to 4.0 mm. Color: White (RHS NN155C) with light greenish-yellow tips (RHS 4C); dotted (RHS 71A).

Reproductive organs:

*Column*.—Length: 9.0 mm to 11.0 mm. Diameter: 3.0 mm to 4.0 mm. Color: Reddish-purple (RHS N78A) at the base and toward the tip (RHS N78B).

*Pollinia*.—Quantity: 2. Diameter: 0.9 mm to 1.1 mm. Color: Orange-yellow (RHS 23A).

*Ovary*.—Length: 10.0 mm to 12.0 mm. Diameter: 1.8 mm to 2.0 mm.

*Pedicel*.—Length: 32.0 mm to 34 .0 mm. Diameter: 2.2 mm to 2.5 mm. Texture: Smooth. Color: Hint of dark purplish-red (RHS N79B) at the base; yellow-green (RHS 195B) and light purple (RHS 77C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGYMA' differs from the female parent plant '01-0269' (unpatented) in that 'PHALGYMA' has calluses with a main color of white, whereas '01-0269' has calluses with a main color of yellow.

'PHALGYMA' differs from male parent plant '33408-09' (unpatented) in that 'PHALGYMA' has weakly spatulate apical lobes and calluses with a main color of white, whereas '33408-09' has spatulate apical lobes and calluses with a main color of yellow. Additionally, 'PHALGYMA' has smaller flowers than '33408-09'.

'PHALGYMA' is most similar to the commercial *Phalaenopsis* plants named 'PHALFROFE' (U.S. Plant Pat. No. 31,979) and 'PHALDONFI' (U.S. Plant Pat. No. 26,066). 'PHALGYMA' differs from the commercial variety 'PHALFROFE' in that 'PHALGYMA' has calluses with a main color of white and apical lobes with a main color of dark purplish-red (RHS N79C) and reddish-purple (something in between RHS N78A and N79C) toward whiskers, whereas 'PHALFROFE' has calluses with a main color of greenish-yellow and apical lobes with a main color of red (RHS 185A) and reddish-purple (RHS NN78A) toward whiskers.

'PHALGYMA' differs from the commercial variety 'PHALDONFI' in that 'PHALGYMA' has calluses with a main color of white, whereas 'PHALDONFI' has calluses with a main color of yellow. Additionally, 'PHALGYMA' has shorter leaves than 'PHALDONFI'.

I claim:

1. A new and distinct variety of *Phalaenopsis* plant named 'PHALGYMA', substantially as described and illustrated herein.

* * * * *